(12) United States Patent
Nardo

(10) Patent No.: US 7,435,388 B2
(45) Date of Patent: Oct. 14, 2008

(54) APPLICATOR OF A FLUID SAMPLE ON A SUBSTRATE

(75) Inventor: Pietro Antonio Nardo, Cusano Milanino (IT)

(73) Assignee: Alfa Wassermann, S.p.A., Alanno Scalo (Pescara) (IT)

(*) Notice: Subject to any disclaimer, the term of this patent is extended or adjusted under 35 U.S.C. 154(b) by 896 days.

(21) Appl. No.: 10/361,213

(22) Filed: Feb. 10, 2003

(65) Prior Publication Data

US 2003/0159934 A1    Aug. 28, 2003

(30) Foreign Application Priority Data

Feb. 25, 2002    (IR) .......................... MI2002A0367

(51) Int. Cl.
*B01L 3/02*    (2006.01)

(52) U.S. Cl. .......................... 422/100; 422/99; 204/456; 204/600; 204/606

(58) Field of Classification Search .................. 422/99, 422/100, 101; 204/451–453, 456, 459, 466, 204/600, 601, 604, 605, 606, 613, 616
See application file for complete search history.

(56) References Cited

U.S. PATENT DOCUMENTS

| | | | |
|---|---|---|---|
| 3,616,387 | A | 10/1971 | Siebert |
| 3,855,846 | A | 12/1974 | Forget |
| 4,086,372 | A | 4/1978 | Golias |

FOREIGN PATENT DOCUMENTS

| | | |
|---|---|---|
| DE | 11 80 166 C | 12/1961 |
| DE | 25 41 965 | 4/1976 |
| DE | 27 04 096 | 8/1978 |
| WO | WO 94 08234 | 4/1994 |
| WO | WO 95 20155 | 7/1995 |
| WO | WO 97/42496 | 11/1997 |

*Primary Examiner*—Jill Warden
*Assistant Examiner*—Dwayne K. Handy
(74) *Attorney, Agent, or Firm*—Bucknam and Archer

(57) ABSTRACT

Applicator of a fluid sample on a substrate, wherein at least an applying blade substantially of rectangular shape in its turn defining a body of the blade, a tip of the blade and two facing side edges of the blade, wherein each blade has a drain of the body of the blade stretching between the facing side edges of the blade, the drain defining a physical barrier for the fluid sample; and at least one calibrated retention aperture of the fluid sample, put between the tip of the blade and the drain of the blade, the at least one aperture being calibrated in order to keep on its inside an exactly defined amount of fluid sample.

10 Claims, 3 Drawing Sheets

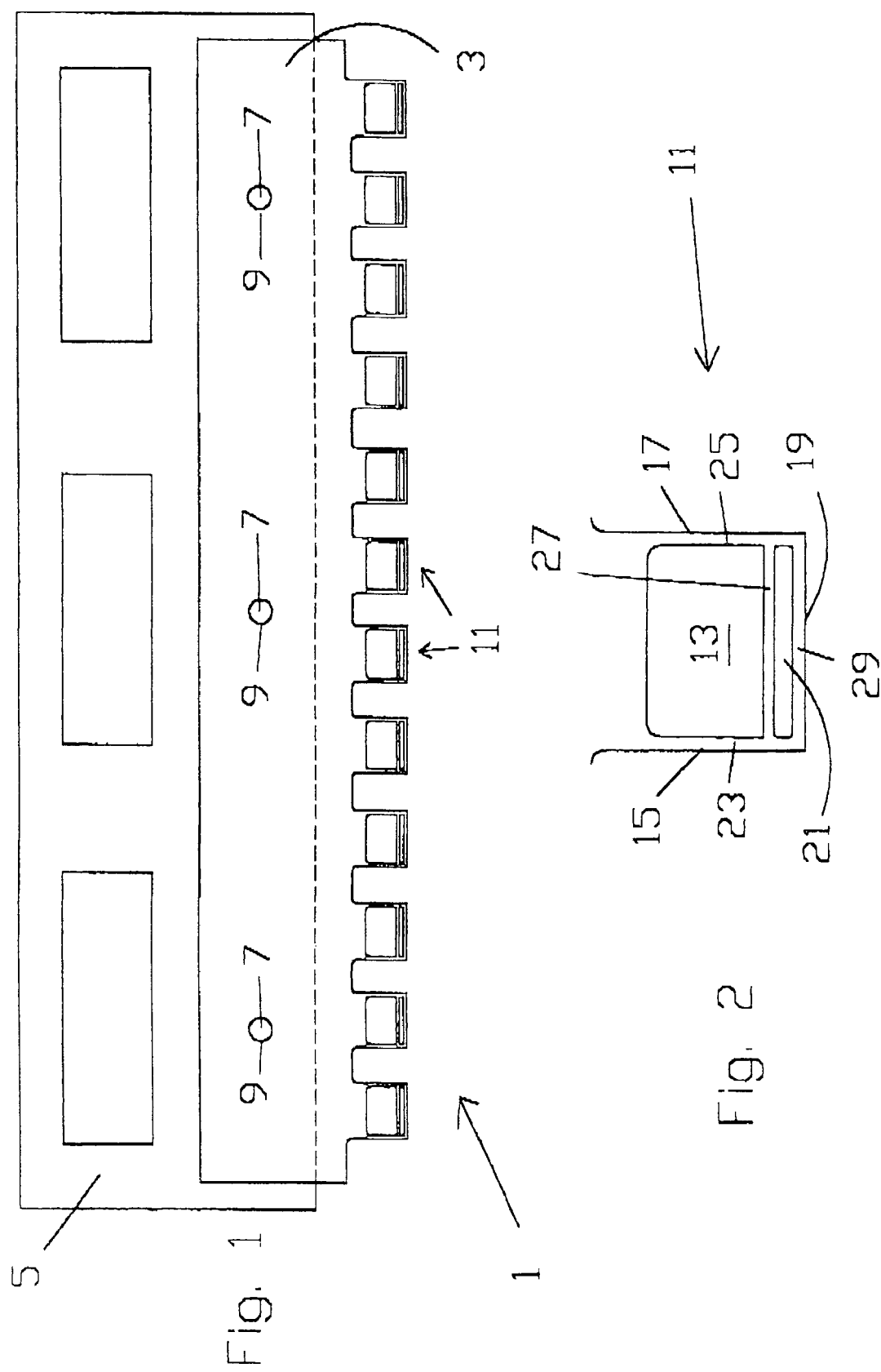

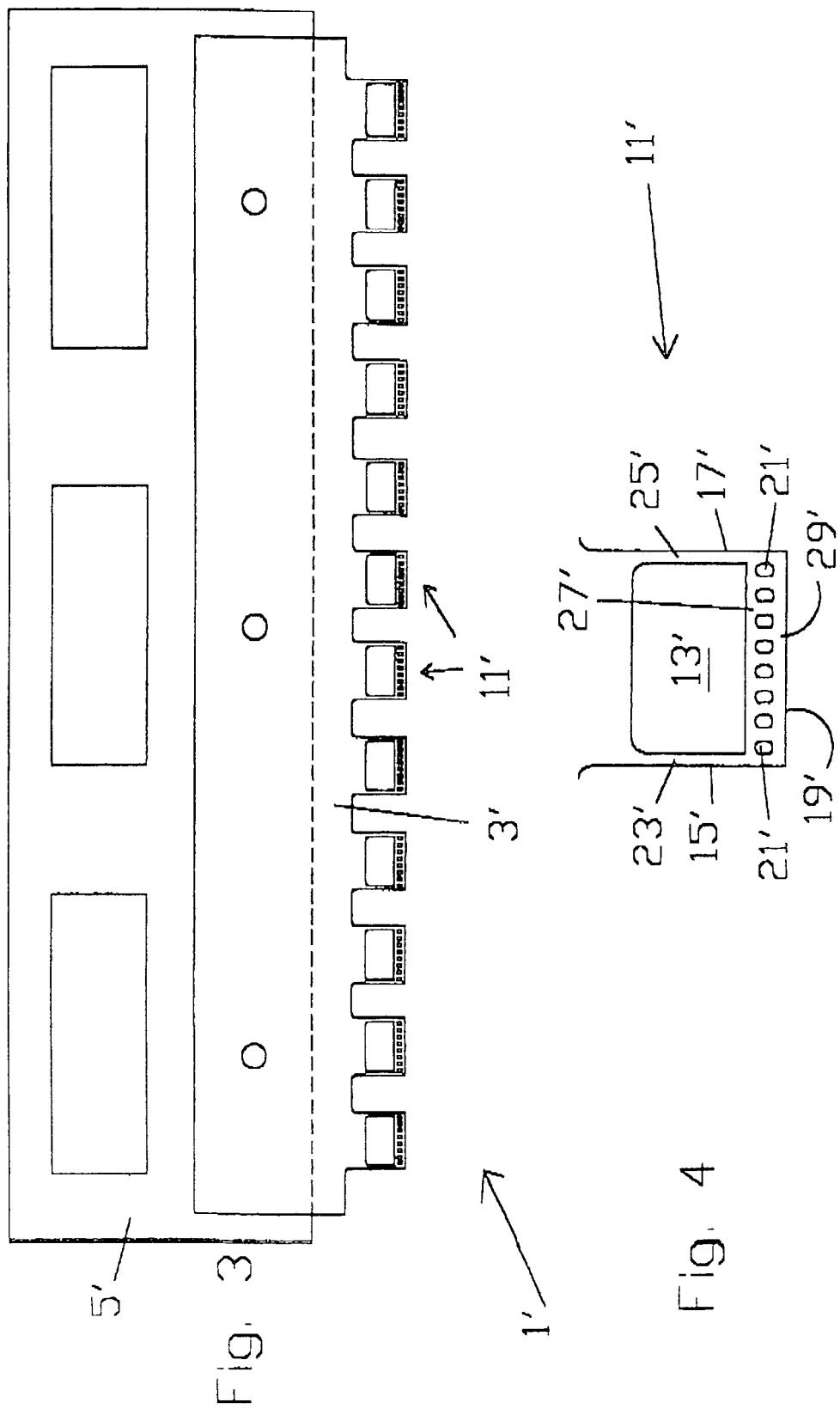

APPLICATOR OF A FLUID SAMPLE ON A SUBSTRATE

BACKGROUND OF THE INVENTION

The present invention refers to an apparatus for applying a fluid sample on a substrate, to be preferably used in the medical and chemical field to carry out analyses of a fluid sample with diagnostic scope, preferably for the electrophoretic test of the fluid sample.

It is known that the result of the electro-phoretic analysis of a fluid sample can be influenced by some factors like the shape, the volume, the amount and the positioning of the fluid sample on the substrate.

Many applicators are known for taking from a tray a little and exactly defined amount, in the order of microliters, of a fluid sample to be transferred on a substrate for the electrophoretic analysis.

The published patent application WO 97/42496 describes an applicator made of a multiplicity of blades wherein each blade provides a barrier for the fluid sample.

In case the barrier is a physical barrier represented by an aperture, each blade of the applicator takes the fluid sample adhered on its portion of surface comprised between the tip of the blade and the aperture of the blade.

Such an applicator shows some drawbacks.

First, the amount taken of the fluid sample is not exactly defined when the applicator is dipped in the taking tray at such a depth that the barrier made on the blades is exceeded, because in such a case the amount of the fluid sample adhered to the blades over the barrier cannot be foreseen.

The amount of fluid sample taken in such applicator can not be exactly defined also because of the fact that the fluid sample in the taking tray can make a meniscus that can prevent the tip of the blades from getting uniformly wet.

In particular, the trays commonly used for such an applicator are equipped with narrow rectangular marks of housing of the rectangular blades of the applicator where the fluid to be sampled makes a meniscus.

Summing up, if the blades of the applicator are dipped too little in the relative marks of the tray and if the meniscus made from the fluid to be sampled in the relative marks of housing of the taking tray is convex, the risk exists that the central portion of the tip of the blades gets wet while the side areas of the blades stay dry, on the contrary if the blades of the applicator are dipped too much in the relative marks the risk exists that also the portion of the blades over the barrier gets wet.

In both cases the amount of fluid sample taken is not exactly defined. Moreover such an applicator can prevent a complete seeding of the fluid sample taken on the substrate.

As a matter of fact, during the penetration of the blades of the applicator into the substrate, a portion of the fluid sample present on the tip of the blades can be pushed towards the surface of the substrate by the action of the edges of the incision of the substrate and so can stay adhered to the blades of the applicator even after the extraction of the applicator from the substrate.

DETAILED DESCRIPTION OF THE INVENTION

To provide for overcoming the drawbacks present in the traditional apparatuses for the application of a fluid sample on a substrate is the scope of the present invention, and in particular a scope is supplying an applicator able to deposit on a substrate an always exactly defined amount of fluid sample.

Further scope of the present invention is to provide an applicator of a fluid sample on a substrate able to make a linear bidimensional deposit of the fluid sample on a substrate.

Further more scope of the present invention is to realize a structurally simple and cheap applicator of a fluid sample.

These scopes are got by means of an applicator of a fluid sample on a substrate, comprising at least one and preferably more applying blades of substantially rectangular shape in its turn defining a body of the blade, a tip of the blade and two facing side edges of the blade, characterised in that each blade comprises:

- a drain of the body of the blade stretching between the facing side edges of the blade, said drain defining a physical barrier for the fluid sample; and
- at least one calibrated retention aperture of the fluid sample, put between the tip of the blade and the drain of the blade, said at least one aperture being calibrated in order to keep on its inside an exactly defined amount of fluid sample.

The drain of the blades of the applicator exactly marks the limits of an area of the blades of the applicator that is provided for the retention of a fluid sample.

The drain of the blades of the applicator avoids an appreciable reascending of fluid by capillarity over the portion of retention of the fluid sample.

The drain of the blades of the applicator avoids anyway every further taking of fluid even in case the blades of the applicator are dipped into the taking tray for a length that goes beyond such an area of retention of the fluid sample.

The sampled fluid is that which trickles by capillarity into the aperture or apertures of the portion of the blades of the applicator of retention of the fluid sample.

Advantageously, during the seeding of the fluid sample on the substrate, the fluid kept back in the retention portion of the blades of the applicator is totally transferred, without any difficulty, on the substrate determining a linear mark of the fluid sample on the substrate.

In particular, the fluid kept back in the aperture or apertures of the retention portion of the blades of the applicator does not meet, during the insertion of the applicator on the substrate, the resistance from the edges of the incisions of the substrate made from the tips of the blades of the applicator, but, on the contrary, it uses, during the extraction of the applicator from the substrate, the resistance given from the edges of the incisions of the substrate made from the tips of the blades of the applicator for keeping the fluid on the substrate.

These advantageous aspects will be clearer further to the following text of preferred modes of carrying out the invention which have to be read as illustrative but not limitative title of the more general claimed principle.

The following description refers to the enclosed drawings wherein:

FIG. 1 is a side upper view of a preferred execution of a multi-blades applicator according to the present invention for the taking of a fluid sample to be analyzed according to an electro-phoretic method;

FIG. 2 is an enlarged view of a blade of the applicator of FIG. 1;

FIG. 3 is a side upper view of a further preferred execution of a multi-blades applicator according to the present invention for the taking of a fluid sample to be analyzed according to an electro-phoretic method;

FIG. 4 is an enlarged view of a blade of the applicator of FIG. 3;

Figure 5:
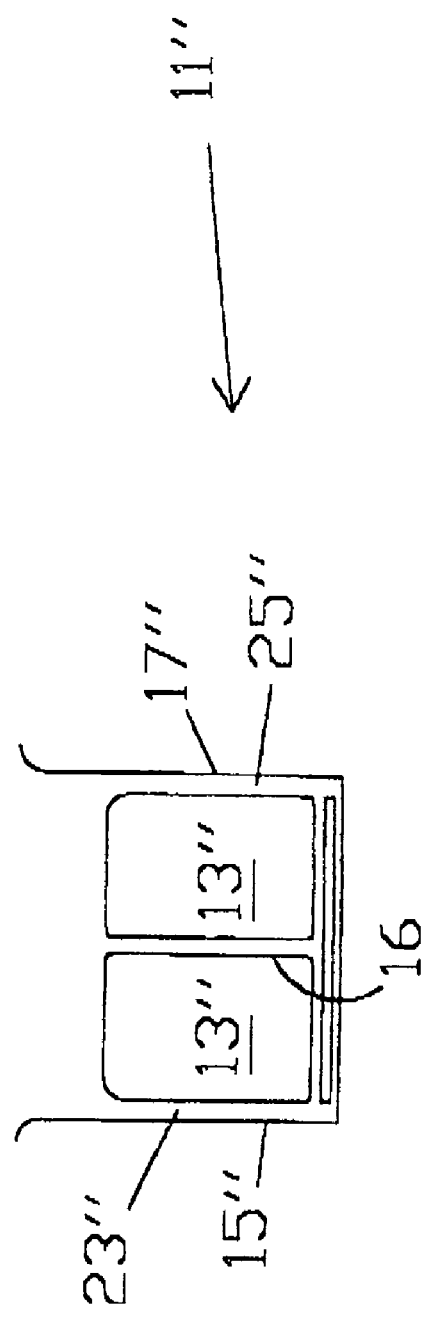
Figure 6:
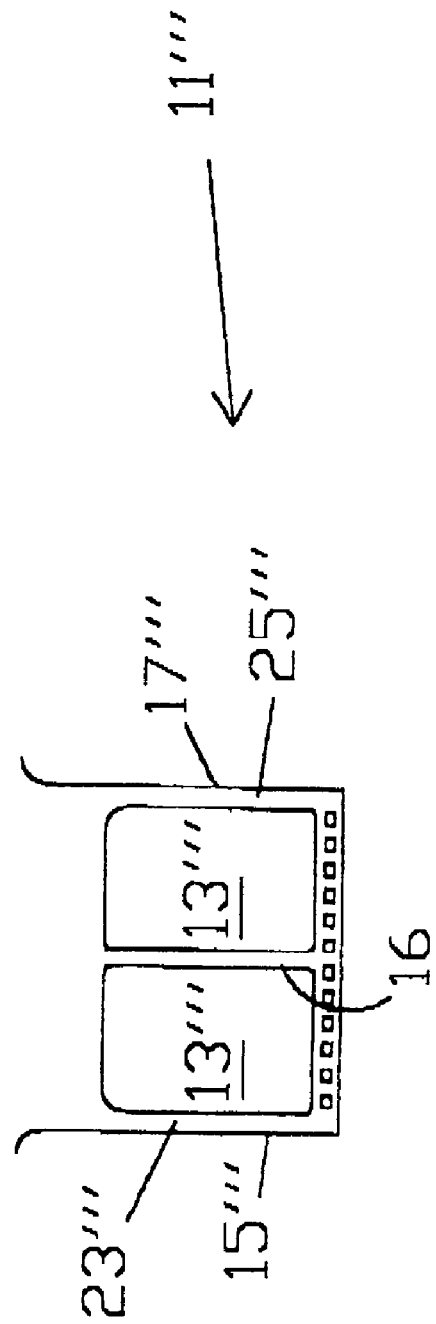

FIG. 5 is an enlarged view of a third preferred execution of a blade of a multi-blades applicator according to the present invention for the taking of a fluid sample to be analyzed according to an electro-phoretic method; and FIG. 6 is an enlarged view of a fourth preferred execution of a multi-blades applicator according to the present invention for the taking of a fluid to be analyzed according to an electro-phoretic method.

EXAMPLE 1

A multi-blades applicator 1 for sampling a fluid to be analyzed in electro-phoretic mode is shown, with reference to FIGS. 1 and 2, comprising a laminar longitudinal body 3 of the applicator 1, and a frame 5 for the support of the body 3 of the applicator 1 having the thickness of some millimeters and an essentially rectangular shape with longitudinal axis parallel to that of the body 3 of the applicator 1.

The body 3 of the applicator is fixed to the frame 5 by gluing or, as illustrated, by means of a series of buttons 7 of the frame 5 pressure-fitted in the respective holes 9 of the body 3 of the applicator 1.

The body of the applicator 3 is preferably made of stainless steel while the frame 5 can also be made of plastic.

The edge of the part of the body 3 of the applicator 1 jutting out from the longitudinal side of the support frame 5 is shaped with a series of identical rectangular applying blades 11 longitudinally aligned.

Each applying blade 11 comprises in correspondence of a portion of inner blade a drain 13 substantially rectangular longitudinally stretching between the facing side edges 15 and 17 of the blade 11 at a fixed distance from the tip 19 of the blade 11, which drain 13 defines a physical barrier for the fluid to be sampled.

Each applying blade 11 further comprises in a position put between the tip 19 of the blade 11 and the drain 13 of the blade 11 a longitudinal calibrated aperture 21 for the retention of a fluid sample.

The drain 13 of the blade 11 and the aperture 21 of the blade 11 are limited by facing side edges 23 and 25 having calibrated width, so as the width of the longitudinal edge 27 which separates the drain 13 of the blade 11 from the aperture 21 of the blade 11 and the width of the longitudinal edge 29 which separates the tip 19 of the blade 11 from the aperture 21 of the blade 11 are also calibrated.

The size preferred for the applicator is as follows.

Each blade 11 has a longitudinal size equal to 4.5 mm and height equal to 4 mm, the drain 13 of each blade 11 has height equal to 2 mm, the aperture 21 of each blade has height equal to 0.25 mm and preferably comprised between 0.2 and 0.3 mm, the facing side edges 23 and 25 of each blade 11 have a width equal to 0.375 mm and preferably comprised between 0.35 and 0.4 mm, the longitudinal edge 27 which separates the drain 13 of each blade 11 from the aperture 21 of each blade 11 has a width equal to 0.1 mm and preferably comprised between 0.05 mm and 0.15 mm, the longitudinal edge 29 which separates the tip 19 of each blade 11 from the aperture 21 of each blade 11 has a width equal to 0.15 mm and preferably comprised between 0.1 mm and 0.2 mm.

EXAMPLE 2

A different form of multi-blades applicator for the sampling of a fluid to be analyzed in an electro-phoretic mode is shown, with reference to FIGS. 3 and 4, whose parts equivalent to those of the applicator shown in FIGS. 1 and 2 will be marked with the same numerical reference followed by an apostrophe.

The applicator 1' comprises a laminar longitudinal body 3' of the applicator 1', and a frame 5' for the support of the body 3' of the applicator 1'.

The edge of the part of the body 3' of the applicator 1' jutting out from the longitudinal side of the support frame 5' is shaped with a series of identical rectangular applying blades 11' longitudinally aligned.

Each applying blade 11' comprises in correspondence of a portion of inner blade a drain 13' substantially rectangular longitudinally stretching between the facing side edges 15' and 17' of the blade 11' at a fixed distance from the tip 19' of the blade 11', which drain 13' defines a physical barrier for the fluid to be sampled.

Each applying blade 11' further comprises in a position put between the tip 19' of the blade 11' and the drain 13' of the blade 11' a series of calibrated apertures 21' longitudinally aligned for the retention of a fluid sample.

The drain 13' of the blade 11' and the series of apertures 21' of the blade 11' are limited by facing side edges 23' and 25' having calibrated width, so as the width of the longitudinal edge 27' which separates the drain 13' of the blade 11' from the series of apertures 21' of the blade 11' and the width of the longitudinal edge 29' which separates the tip 19' of the blade 11' from the series of apertures 21' of the blade 11' are also calibrated.

The size preferred for the applicator is as follows.

Each blade 11' has a longitudinal size equal to 4.5 mm and height equal to 4 mm, the drain 13' of each blade 11' has height equal to 2 mm, the apertures 21' of each blade have height equal to 0.3 mm and preferably comprised between 0.25 and 0.35 mm, width equal to 0.15 mm and preferably comprised between 0.1 mm and 0.2 mm, and distance between centres equal to 0.3 mm and preferably comprised between 0.25 mm and 0.35 mm, the facing side edges 23' and 25' of each blade 11' have a width equal to 0.375 mm and preferably comprised between 0.35 and 0.4 mm, the longitudinal edge 27' which separates the drain 13' of each blade 11' from the apertures 21' of each blade 11' has a width equal to 0.1 mm and preferably comprised between 0.05 mm and 0.15 mm, the longitudinal edge 29' which separates the tip 19' of each blade 11' from the apertures 21' of each blade 11' has a width equal to 0.15 mm and preferably comprised between 0.1 mm and 0.2 mm.

EXAMPLE 3

A third and respectively a fourth form of blade of multi-blades applicator for the sampling of a fluid to be analyzed in an electro-phoretic mode are shown, with reference now to FIGS. 5 and respectively 6, whose parts equivalent to those of the blade shown in FIGS. 2 and respectively 4 will be marked with the same numerical reference followed by two and respectively three apostrophes.

The applying blade 11'' of FIG. 5 differs from that of FIG. 2 only because of the fact that the drain 13'' of the blade 11'' now is subdivided into two equal parts separated by a central calibrated edge 16 stretching parallely to the side facing edges 15'' and 17'' of the blade 11'' and sized in width like the side facing edges 23'' and 25'' of the blade 11''.

Similarly, the applying blade 11''' of FIG. 6 differs from that of FIG. 4 only because of the fact that the drain 13''' of the blade 11''' now is subdivided into two equal parts separated by a central edge 16 stretching parallely to the side facing edges 15''' and 17''' of the blade 11''' and sized in width like the side facing edges 23''' and 25''' of the blade 11'''.

The invention claimed is:

1. Applicator of a fluid sample on a substrate, comprising at least an applying blade of substantially rectangular shape in its turn defining a body of the blade, a tip of the blade and two facing side edges of the blade, wherein the blade comprises:
- a drain of the body of the blade extending between the facing side edges of the blade, said drain defining a physical barrier for the fluid sample;
- at least one calibrated retention aperture of the fluid sample, said at least one retention aperture being disposed between the tip of the blade and the drain of the blade and being calibrated so as to retain on its inside an exactly defined amount of fluid sample, wherein said drain is at least about six and two thirds times larger in area than said at least one retention aperture; and
- a longitudinal edge having calibrated width which separates the drain of the blade from said at least one retention aperture of the blade.

2. Applicator of a fluid sample on a substrate according to claim 1, wherein said drain of the blade has substantially rectangular shape.

3. Applicator of a fluid sample on a substrate according to claim 1, wherein said drain of the blade is subdivided into two parts separated by a central edge parallel to the side edges of the blade and having calibrated width.

4. Applicator of a fluid sample on a substrate according to claim 1, wherein the two facing edges of the body of the blade have calibrated width which laterally limit the drain of the blade.

5. Applicator of a fluid sample on a substrate according to claim 1, wherein the body of the blade defines an edge having calibrated width between the tip of the blade and said at least one aperture of the blade.

6. Applicator of a fluid sample on a substrate according to claim 1, which comprises one calibrated aperture extending between the facing side edges of the blade parallel to the tip of the blade.

7. Applicator of a fluid sample on a substrate according to claim 1, which comprises a series of calibrated apertures aligned parallel to the tip of the blade.

8. Applicator of a fluid sample on a substrate according to claim 1, wherein the body of the applicator is made of stainless steel.

9. Applicator of a fluid sample on a substrate according to claim 1, wherein the applicator is used in the etectro-phoretic analysis of the fluid sample.

10. Applicator of a fluid sample on a substrate according to claim 1, which comprises a multiplicity of blades aligned along a longitudinal axis of the applicator.

* * * * *